United States Patent
You et al.

(10) Patent No.: US 11,242,552 B2
(45) Date of Patent: Feb. 8, 2022

(54) NUCLEIC ACID INTEGRATED DETECTION METHOD AND DETECTION REAGENT TUBE

(71) Applicant: USTAR Biotechnologies (Hangzhou) Ltd., Hangzhou (CN)

(72) Inventors: Qimin You, Hangzhou (CN); Lin Hu, Hangzhou (CN); Chen Qi, Hangzhou (CN); Junwei Yu, Hangzhou (CN); Zhujun Yu, Hangzhou (CN); Sha Wang, Hangzhou (CN); Rongyu Jin, Hangzhou (CN); Daisang Wang, Hangzhou (CN); Sisi Chen, Hangzhou (CN); Junli He, Hangzhou (CN); Jing Chen, Hangzhou (CN); Huanxin Rao, Hangzhou (CN); Yanqiong Zhou, Hangzhou (CN); Fan Yang, Hangzhou (CN)

(73) Assignee: USTAR Biotechnologies (Hangzhou) Ltd., Hangzhou (CN)

( * ) Notice: Subject to any disclaimer, the term of this patent is extended or adjusted under 35 U.S.C. 154(b) by 0 days.

(21) Appl. No.: 17/044,734

(22) PCT Filed: Feb. 1, 2019

(86) PCT No.: PCT/CN2019/074312
§ 371 (c)(1),
(2) Date: Oct. 1, 2020

(87) PCT Pub. No.: WO2020/001030
PCT Pub. Date: Jan. 2, 2020

(65) Prior Publication Data
US 2021/0155974 A1 May 27, 2021

(30) Foreign Application Priority Data
Jun. 26, 2018 (CN) .......................... 201810669579.9

(51) Int. Cl.
*C12Q 1/68* (2018.01)
*C12Q 1/6806* (2018.01)
*B01J 19/00* (2006.01)

(52) U.S. Cl.
CPC ........ *C12Q 1/6806* (2013.01); *B01J 19/0046* (2013.01); *B01J 2219/00292* (2013.01);
(Continued)

(58) Field of Classification Search
CPC ......... B01L 2300/087; B01L 3/502761; B01L 2200/0647; B01L 2200/10;
(Continued)

(56) References Cited

U.S. PATENT DOCUMENTS

2007/0292858 A1* 12/2007 Chen ...................... B01L 3/502
435/6.18
2013/0273552 A1* 10/2013 Ohashi ..................... B03C 1/288
435/6.12
(Continued)

FOREIGN PATENT DOCUMENTS

CN 105349530 2/2016
CN 105349530 A 2/2016
(Continued)

OTHER PUBLICATIONS

"International Application No. PCT/CN2019/074312, International Search Report and Written Opinion dated Jan. 17, 2020", (w/ English Translation), (dated Jan. 17, 2020), 9 pgs.

*Primary Examiner* — Betty J Forman
(74) *Attorney, Agent, or Firm* — Schwegman Lundberg & Woessner, P.A.

(57) ABSTRACT

A nucleic acid integrated detection method and detection reagent tube are provided, separating a lysis solution, a cleaning solution and a reaction solution in a detection reagent tube by providing a plurality of separation plugs in
(Continued)

an over-under arrangement and disposing a hydrophobic layer in liquid or solid phase on each separation plug; adding a sample into the lysis solution; extracting nucleic acid in the sample using magnetic nanobeads; and then driving the magnetic nanobeads carrying the nucleic acid to sequentially pass through each hydrophobic layer along a magnetic bead channel and into the cleaning solution and the reaction solution to realize a cleaning and amplification for the nucleic acid, and finally, detecting the nucleic acid of the sample by an external device using an optical detection method, thus realizing a plurality of steps of nucleic acid extraction, cleaning and amplification reactions in the same detection reagent tube.

15 Claims, 5 Drawing Sheets

(52) U.S. Cl.
CPC ............... *B01J 2219/00299* (2013.01); *B01J 2219/00349* (2013.01); *B01J 2219/00414* (2013.01); *B01J 2219/00418* (2013.01); *B01J 2219/00702* (2013.01); *C12Q 2563/149* (2013.01)

(58) Field of Classification Search
CPC .......... B01L 2300/0864; C12Q 1/6806; C12Q 2563/149; B01J 19/00414; B01J 19/00418; B01J 19/0046; B01J 2219/00281; B01J 2219/00299; B01J 2219/00702; B01J 2019/00292; C12N 15/1003
See application file for complete search history.

(56) References Cited

U.S. PATENT DOCUMENTS

2015/0118743 A1* 4/2015 Hanamura ......... C12N 15/1003
435/293.1
2019/0376121 A1 12/2019 Song et al.

FOREIGN PATENT DOCUMENTS

| CN | 107151700 | 9/2017 |
| CN | 107151700 A | 9/2017 |
| WO | WO2020001030 | 1/2020 |
| WO | WO-2020001030 A2 | 1/2020 |

\* cited by examiner

NUCLEIC ACID INTEGRATED DETECTION METHOD AND DETECTION REAGENT TUBE

PRIORITY CLAIM TO RELATED APPLICATIONS

This application is a U.S. national stage filing under 35 U.S.C. § 371 from International Application No. PCT/CN2019/074312, filed on 1 Feb. 2019, and published as WO2020/001030 on 2 Jan. 2020, which claims the benefit under 35 U.S.C. 119 to Chinese Application No. 201810669579.9, filed on 26 Jun. 2018, the benefit of priority of each of which is claimed herein, and which applications and publication are hereby incorporated herein by reference in their entirety.

TECHNICAL FIELD

The invention relates to a nucleic acid detection method and a reagent tube, in particular to a nucleic acid integrated detection method and a detection reagent tube.

BACKGROUND ART

Laboratory nucleic acid detection has a short cycle and its sensitivity and specificity is comparable with that of a culture method; at present, a nucleic acid detection reagent tube is usually used in the nucleic acid detection for a sample. In existing nucleic acid detection tubes, a lysis solution, a cleaning solution and a reaction solution are usually separated by solid separation layers which are then heated and melt so that magnetic beads carrying nucleic acid can pass through the separation layers for corresponding operations. However, the nucleic acid is sensitive to changes in temperature, thus an operator needs to strictly control a heating area to reduce influence of the changes in temperature on nucleic acid, which will increase operation difficulty. Meanwhile, the existing detection tubes are easily interfered by many factors (for example, the interference of temperature on nucleic acid), resulting in a large error in an existing detection result. Therefore, it exists problems of a large detection error and a large operational difficulty for existing technologies.

SUMMARY

An object of the present invention is to provide a nucleic acid integrated detection method and a detection reagent tube. The invention presents advantages of reduced detection errors and operational difficulty.

According to a technical scheme of the invention, a nucleic acid integrated detection method is provided, including: separating a lysis solution, a cleaning solution and a reaction solution in a detection reagent tube by providing a plurality of separation plugs arranged one above one another and disposing a hydrophobic layer in a liquid or a solid phase at each separation plug; adding a sample into the lysis solution for mixing and lysis; extracting a nucleic acid in the sample using magnetic nanobeads; and then driving, by an external magnet, the magnetic nanobeads carrying the nucleic acid to sequentially pass through each hydrophobic layer along a magnetic bead channel in an inner wall of the detection reagent tube and into the cleaning solution and the reaction solution to realize a cleaning and amplification for the nucleic acid, wherein a biological agent required in the reaction solution is stored in a separation plug above the reaction solution; and finally, detecting the nucleic acid of the sample by an external device using an optical detection method, thus realizing a plurality of steps of nucleic acid extraction, cleaning and amplification reaction in the same detection reagent tube.

In the aforementioned nucleic acid integrated detection method, one or more branch tubes are provided at a lower part of the detection tube, the amplification reaction is performed in each branch tube, and one or more clusters of magnetic nanobeads carrying the nucleic acid are driven into the one or more branch tubes by the external magnet to react independently, so that nucleic acid from one sample can be simultaneously detected in one or more different reaction systems.

In the aforementioned nucleic acid integrated detection method, a reagent storage chamber with a downward opening is disposed in the separation plug above the reaction solution, a biochemical reagent is disposed in the reagent storage chamber, the biochemical reagent is stored on a carrier, and is sealed and protected by a hydrophobic sealing layer in the reagent storage chamber.

In the aforementioned nucleic acid integrated detection method, the biochemical reagent is stored on a magnetic carrier and sealed and protected by the hydrophobic sealing layer in the reagent storage chamber; when the reaction is needed, the biological reagent is driven by the external magnet to pass through the hydrophobic sealing layer and into the reaction solution, thus realizing the transferring of the biochemical reagent from the reagent storage chamber to the reaction solution.

In the aforementioned nucleic acid integrated detection method, the biochemical reagent is stored on the carrier and sealed and protected by the hydrophobic sealing layer composed of a hot melt substance; when the reaction is needed, the separation plug is heated in a temperature control mode, in which the hot melt substance is heated and melted so that the biochemical reagent in the storage chamber can move out, thus realizing the transferring of the biochemical reagent from the reagent storage chamber to the reaction solution.

A nucleic acid integrated detection reagent tube includes a main tube, and one or more branch tubes are provided at a lower end of the main tube, wherein a lysing zone, a first separation plug, a cleaning zone and a second separation plug are sequentially disposed from top to bottom in the main tube, a reaction zone is provided in each branch tube and the second separation plug is positioned at a connection between the one or more branch tubes and the main tube; a reagent storage chamber with a downward opening is disposed in the second separation plug, a carrier for storing reagents is disposed in the reagent storage chamber and a hydrophobic sealing layer is also provided in the reagent storage chamber; hydrophobic layers in a liquid or a solid phase are disposed at both the first separation plug and the second separation plug; and a magnetic bead channel penetrating to the one or more branch tubes is also defined in an inner wall of the main tube.

In the aforementioned nucleic acid integrated detection reagent tube, a magnetizable mixing device is provided in the reaction zone and/or the cleaning zone.

In the aforementioned nucleic acid integrated detection reagent tube, the first separation plug comprises a plug wherein a tapered surface is provided on an upper end of the plug and a bump is provided above the tapered surface.

In the aforementioned nucleic acid integrated detection reagent tube, a plurality of arc-shaped convex surfaces are provided on a side wall of the plug and a channel is provided between adjacent arc-shaped convex surfaces.

In the aforementioned nucleic acid integrated detection reagent tube, the second separation plug includes a partition plate, wherein a plurality of plug bodies corresponding to positions of the one or more branch tubes are arranged below the partition plate, a protrusion is arranged on an upper end of the partition plate; and a reagent storage chamber is disposed in each plug body.

Compared with the prior art, according to the present invention, the lysis solution, the cleaning solution and the reaction solution in the detection reagent tube are separated by mutually cooperatively arranging a plurality of separation plugs and hydrophobic layers in a liquid or a solid phase, and the magnetic nanobeads are driven by the external magnet to move along the magnetic bead channel without any heating required for the detection reagent tube during the whole movement process of the magnetic nanobeads, thus not only simplifying the operation and reducing the operational difficulty, but also reducing the interference of temperature on nucleic acid, effectively improving the detection accuracy and reducing the errors; meanwhile, all reactions are concentrated in one detection reagent tube, which can effectively avoid pollution and cross contamination and improve detection accuracy. According to the invention, the lysis solution and the cleaning solution are placed in the main tube and the reaction solution in the branch tubes so that nucleic acid can enter into different branch tubes respectively after being cleaned, enabling nucleic acid entering into different branch tubes to be with the same state, which results in reduced interference and detection errors. According to the invention, the reagent storage chamber is arranged in the separation plug (i.e. the second separation plug) above the reaction solution, and a dry environment for storing the biochemical reagent is provided through the mutual cooperation of the hydrophobic layer in liquid or solid phase with the hydrophobic sealing layer in the reagent storage chamber, so that the reduced stability of biochemical reagent after being subjected to moisture can be effectively prevented, a better storage can be presented due to a packaging effect of the hydrophobic layer, and a better redissolution effect also can be obtained by using the magnetic or non-magnetic carrier as a biochemical reagent attachment, thereby effectively improving detection accuracy and reducing errors. In summary, the invention presents advantages of reduced detection errors and operational difficulty.

In addition, according to the present invention, the reagent storage chamber is arranged in the second separation plug and the hydrophobic sealing layer composed of a hot melt substance is arranged in the reagent storage chamber, so that the transfer of the biochemical reagent can be performed in a temperature control mode, and an elution and redissolution of nucleic acid can be made in different steps so as to facilitate a more thorough elution for the nucleic acid, thus effectively improving the utilization of samples and the effect of the nucleic acid amplification reaction;

A narrow channel for storing hydrophobic substance is formed between the first separation plug and the tube wall of the reagent tube, so that both a better fixing of the first separation plug and a good separation effect can be realized.

Figure 1:
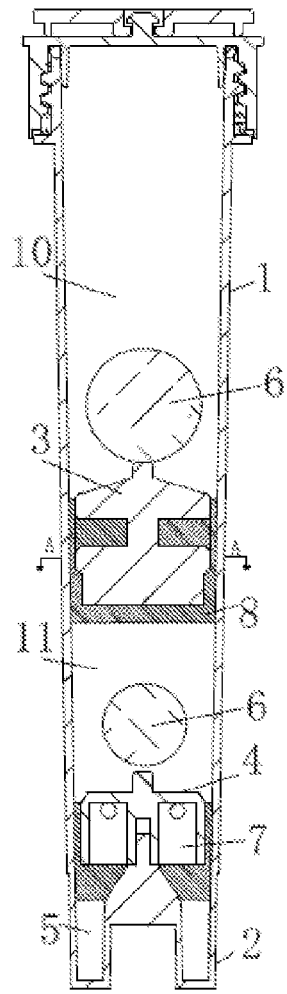
FIG. 1 is a cross-section view of the present invention.

Reference numbers in the drawings are as follows: 1—Main Tube, 2—Branch Tube, 3—First Separation Plug, 4—Second Separation Plug, 5—Reaction Zone, 6—Mixing Device, 7—Reagent Storage Chamber, 8—Hydrophobic Layer, 9—Magnetic Bead channel, 10—Lysing Zone, 11—Cleaning Zone, 12—Carrier, 13—Hydrophobic Sealing Layer, 301—Plug, 302—Tapered Surface, 303—Bump, 304—Rib, 305—Channel, 306—Arc-shaped convex surface, 307—Annular Groove, 401—Partition Plate, 402—Plug Body, 403—Protrusion.

DETAILED DESCRIPTION OF PREFERRED EMBODIMENTS

In the following, the invention will be further explained with reference to the drawings and embodiments, but not as a basis for limiting the invention.

Embodiment 1. A nucleic acid integrated detection method is provided, which includes the following steps of: separating a lysis solution, a cleaning solution and a reaction solution in a detection reagent tube by providing a plurality of separation plugs arranged one above one another and disposing a hydrophobic layer in a liquid or a solid phase at each separation plug; adding a sample into the lysis solution for mixing and lysis; extracting a nucleic acid in the sample using magnetic nanobeads; and then driving, by an external magnet, the magnetic nanobeads carrying the nucleic acid to sequentially pass through each hydrophobic layer along a magnetic bead channel in an inner wall of the detection reagent tube and into the cleaning solution and the reaction solution to realize a cleaning and amplification for the nucleic acid, in which a biological agent required in the reaction solution is stored in a separation plug above the reaction solution; and finally, detecting the nucleic acid of the sample by an external device using an optical detection method, thus realizing a plurality of steps of nucleic acid extraction, cleaning and amplification reactions in the same detection reagent tube.

One or more branch tubes are provided at a lower part of the detection tube, in which the reaction solution is arranged in the branch tubes, the amplification reaction is performed in each branch tube, and one or more clusters of magnetic nanobeads carrying the nucleic acid are driven into the one or more branch tubes by the external magnet to react independently, so that nucleic acid from one sample can be simultaneously detected in one or more different reaction systems. The separation plug and the hydrophobic layer are arranged above the reaction solution to ensure that the nucleic acid entering each branch tube has the same state.

A reagent storage chamber with a downward opening is disposed in the separation plug above the reaction solution, and a biochemical reagent is disposed in the reagent storage chamber, stored on a carrier, and sealed and protected by a hydrophobic sealing layer in the reagent storage chamber.

The biochemical reagent is stored on a magnetic carrier and sealed and protected by a hydrophobic sealing layer in the reagent storage chamber; when the reaction is needed, the biological reagent is driven by the external magnet to pass through the hydrophobic sealing layer and the hydrophobic layer in liquid or solid phase and into the reaction solution, thus realizing the transferring of the biochemical reagent from the reagent storage chamber to the reaction solution.

Figure 2:
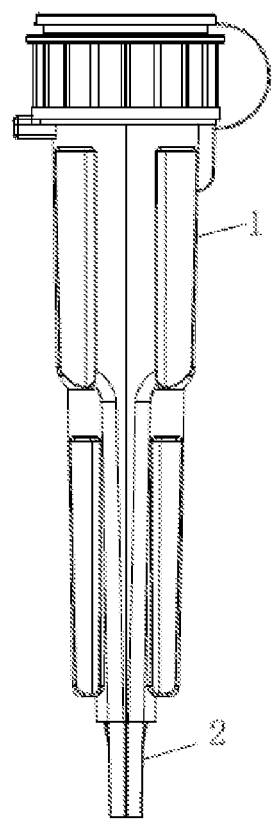
FIG. 2 is a side view of the present invention.
Figure 3:
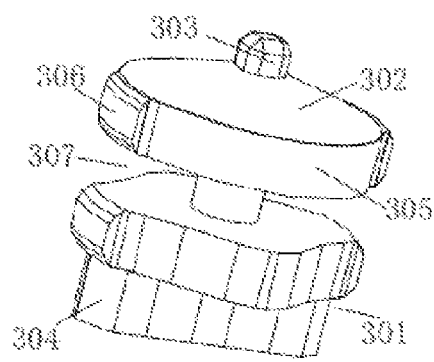
FIG. 3 is a schematic structural view of the first separation plug.
Figure 4:
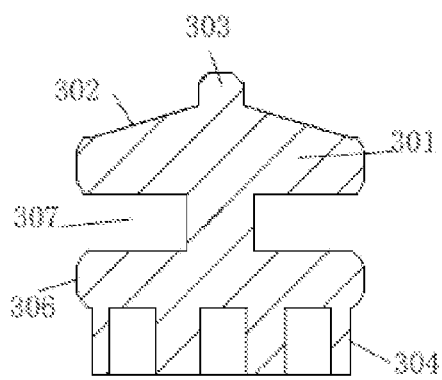
FIG. 4 is a cross-section view of the first separation plug.
Figure 5:
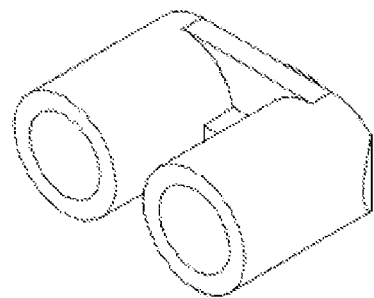
FIG. 5 is a schematic structural view of the second separation plug.
Figure 6:
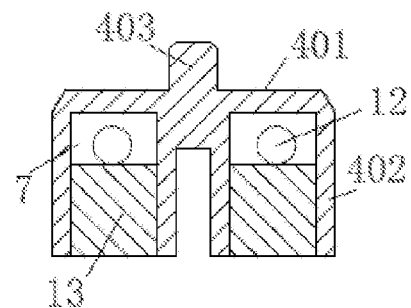
FIG. 6 is a cross-section view of the second separation plug in embodiment 1.
Figure 8:
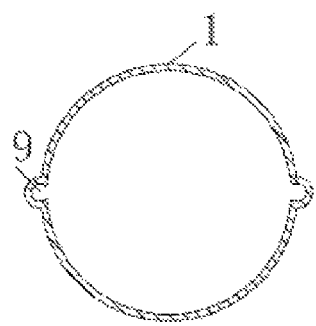
FIG. 8 is a cross-section view taken along line A-A in FIG. 1.

A nucleic acid integrated detection reagent tube which is shown in FIGS. 1-6 and 8 includes a main tube 1 at a lower end of which one or more branch tubes 2 are provided, in which a lysing zone 10, a first separation plug 3, a cleaning zone 11 and a second separation plug 4 are sequentially disposed from top to bottom in the main tube 1, a reaction zone 5 is provided in the branch 2 and the second separation 4 plug is positioned at a connection between the branch tubes 2 and the main tube 1; a reagent storage chamber 7 with a downward opening is defined in the second separation plug 4, a carrier 12 for storing reagents is disposed in the reagent storage chamber and a hydrophobic sealing layer 13 is also provided therein; hydrophobic layers 8 in liquid or solid phase are provided on both the first 3 and the second 4 separation plug; and a magnetic bead channel 9 penetrating to the branch tubes 2 is also defined in the inner wall of the main tube 1.

A magnetizable mixing device 6 is provided in the reaction zone 5 and/or the cleaning zone 11.

Magnetic nanobeads and the magnetizable mixing device 6 can be added to the lysing zone during use.

The first separation plug 3 includes a plug 301, a tapered surface 302 is provided on an upper end of the plug 301 and a bump 303 is provided above the tapered surface 302, and a rib 304 is provided at a lower end of the plug 301.

A plurality of arc-shaped convex surfaces 306 are provided on the side wall of the plug 301 and a channel 305 is provided between adjacent arc-shaped convex surfaces 306. A closed narrow passage is formed between the channel in the side surface of the plug and the side wall of the reagent tube, and the narrow passage is used for separating an upper aqueous solution and a lower aqueous solution by storing hydrophobic substance therein so as to ensure a liquid separation and allow nucleic acid to pass through;

One or more annular grooves 307 are provided in a middle of the plug 301, and the one or more annular grooves divide the plug into two or more layers.

The second separation plug 4 includes a partition plate 401, a plurality of plug bodies 402 corresponding to the positions of the branch tubes 2 are arranged below the partition plate 401 and a protrusion 403 is arranged on an upper end of the partition plate 401; and a reagent storage chamber 7 is defined in each plug body 402.

The main tube 1 is in a conical structure with a larger top and a smaller bottom, and a diameter of an upper end of the main tube 1 is larger than that of its lower end.

A carrier 12 is provided in the reagent storage chamber 7 and the carrier is a magnetic one which is packaged by the biochemical reagent. The reagent storage chamber 7 is also padded with a hydrophobic sealing layer. The hydrophobic sealing layer can be composed of a hot melt substance, such as hot melt paraffin.

A magnetizable mixing device controlled by an external magnet is used in the lysis solution to well mix samples.

A magnetizable mixing device is disposed in the lysis solution and a magnetizable mixing device is also disposed in the reaction solution and/or the cleaning solution, so as to improve a mixing in each region.

An arc-shaped protrusion is provided in a side wall of the rib. Rib is provided with a plurality of cavities with downward openings, and the biochemical reagent is stored in the cavities.

The reaction in the reaction solution is PCR or an isothermal amplification reaction.

The hydrophobic layer is in liquid or solid phase. The hydrophobic layer in liquid phase may be silicone oil and the one in solid phase may be hot melt paraffin. When the magnetic nanobeads need to pass through the hydrophobic layer in solid phase, the hydrophobic layer in solid phase is heated so that paraffin is in a hot melt state.

A positioning groove is provided between the plug bodies, and a positioning boss corresponding to the positioning groove are provided between the branch tubes; the positioning boss includes a conical protrusion arranged between branch tubes, and a positioning block is provided at the upper end of the conical protrusion.

Embodiment 2. A nucleic acid integrated detection method is provided, which includes the following steps of: separating a lysis solution, a cleaning solution and a reaction solution in a detection reagent tube by providing a plurality of separation plugs arranged one above one another and disposing a hydrophobic layer in a liquid or a solid phase at each separation plug; adding a sample into the lysis solution for mixing and lysis; extracting nucleic acid in the sample using magnetic nanobeads; and then driving, by an external magnet, the magnetic nanobeads carrying the nucleic acid to sequentially pass through each hydrophobic layer along a magnetic bead channel in an inner wall of the detection reagent tube and into the cleaning solution and the reaction solution to realize a cleaning and amplification for the nucleic acid, in which a biological agent required in the reaction solution is stored in a separation plug above the reaction solution; and finally, detecting the nucleic acid of the sample by an external device using an optical detection method, thus realizing a plurality of steps of nucleic acid extraction, cleaning and amplification reactions in the same detection reagent tube.

One or more branch tubes are provided at the lower part of the detection tube, the reaction solution is arranged in the branch tubes, the amplification reaction is performed in the branch tubes, and one or more clusters of magnetic nanobeads carrying the nucleic acid are driven into the one or more branch tubes by the external magnet to react independently, so that nucleic acid from one sample can be simultaneously detected in one or more different reaction systems. The separation plug and the hydrophobic layer are arranged above the reaction solution to ensure that the nucleic acid entering each branch tube has the same state.

A reagent storage chamber with a downward opening is disposed in the separation plug above the reaction solution, and the biochemical reagent is disposed in the reagent storage chamber, stored on a carrier, and sealed and protected by a hydrophobic sealing layer in the reagent storage chamber.

The biochemical reagent is stored on the carrier (magnetic or non-magnetic) and sealed and protected by a hydrophobic sealing layer composed of a hot melt substance; when the reaction is needed, the separation plug is heated in a temperature control mode, in which the hot melt substance is heated and melted so that the biochemical reagent in the storage chamber can move out and pass through the hydrophobic layer by the gravity of the carrier. The transferring of the biochemical reagent from the reagent storage chamber to the reaction solution thus can be realized.

Figure 7:
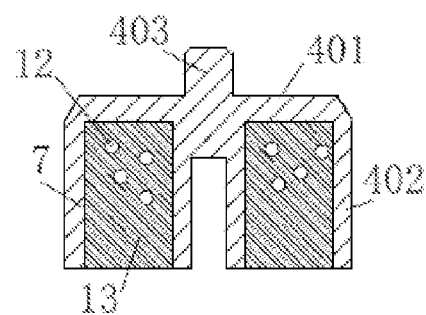
FIG. 7 is a cross-section view of the second separation plug in embodiment 2.

A nucleic acid integrated detection reagent tube which is shown in FIGS. 1-5 and 7-8 includes a main tube 1 at a lower end of which one or more branch tubes 2 are provided, in which a lysing zone 10, a first separation plug 3, a cleaning zone 11 and a second separation plug 4 are sequentially disposed from top to bottom in the main tube 1, a reaction zone 5 is provided in the branch tube 2 and the second separation 4 plug is positioned at a connection between the branch tubes 2 and the main tube 1; a reagent storage chamber 7 with a downward opening is defined in the second separation plug 4, a carrier 12 for storing reagents is disposed in the reagent storage chamber and a hydrophobic sealing layer 13 is also provided therein; hydrophobic layers 8 in liquid or solid phase are provided on both the first 3 and the second 4 separation plug; and a magnetic bead channel 9 penetrating to the branch tubes 2 is also defined in the inner wall of the main tube 1.

The hydrophobic sealing layer 13 is composed of a hot melt substance. The hot melt substance may be hot melt paraffin.

A magnetizable mixing device 6 is provided in the reaction zone 5 and/or the cleaning zone 11.

Magnetic nanobeads and the magnetizable mixing device 6 can be added to the lysing zone during use.

The first separation plug 3 includes a plug 301, a tapered surface 302 is provided on an upper end of the plug 301 and a bump 303 is provided above the tapered surface 302, and a rib 304 is provided at a lower end of the plug 301.

A plurality of arc-shaped convex surfaces 306 are provided on the side wall of the plug 301 and a channel 305 is provided between adjacent arc-shaped convex surfaces 306. A closed narrow passage is formed between the channel in the side surface of the plug and the side wall of the reagent tube, and the narrow passage is used for separating upper and lower aqueous solutions by storing hydrophobic substance therein so as to ensure a liquid separation and allow nucleic acid to pass through;

One or more annular grooves 307 are provided in the middle of the plug 301, and the one or more annular grooves divide the plug into two or more layers.

The second separation plug 4 includes a partition plate 401, in which a plurality of plug bodies 402 corresponding to the positions of the branch tubes 2 are arranged below the partition plate 401 and a protrusion 403 is arranged on an upper end of the partition plate 401; and a reagent storage chamber 7 is defined in each plug body 402.

The main tube 1 is in a conical structure with a larger top and a smaller bottom, and a diameter of an upper end of the main tube 1 is larger than that of its lower end.

A magnetizable mixing device controlled by an external magnet is used in the lysis solution to well mix samples.

A magnetizable mixing device is arranged in the lysis solution and a magnetizable mixing device is also arranged in the reaction solution and/or the cleaning solution, so as to improve a mixing in each region.

An arc-shaped protrusion is provided in a side wall of the rib. Ribs are provided with a plurality of cavities with downward openings, and the biochemical reagent is stored in the cavities.

The reaction in the reaction solution is PCR or an isothermal amplification reaction.

The hydrophobic layer is in liquid or solid phase. The hydrophobic layer in liquid phase may be silicone oil and the one in solid phase may be hot melt paraffin. When the magnetic nanobeads need to pass through the hydrophobic layer in solid phase, the hydrophobic layer in solid phase is heated so that paraffin is in a hot melt state.

A separation layer is provided in the reagent storage chamber.

A positioning groove is provided between the plug bodies, and a positioning boss corresponding to the positioning groove are provided between the branch tubes; the positioning boss includes a conical protrusion arranged between branch tubes, and a positioning block is provided at the upper end of the conical protrusion.

The magnetic carrier may include iron beads, magnetic beads or steel balls, etc., and the non-magnetic carrier can be glass beads or glue beads, etc.

The assembly process of the detection reagent tube is as follows: firstly disposing the reaction solution in the branch tubes, padding the hydrophobic layer, then disposing the second separation plug to match the positioning block with the positioning groove of the second separation plug, then sequentially placing the cleaning solution, the hydrophobic layer and the first separation plug in the main tube, and sealing with paraffin above the first separation plug and capping the tube.

The detection process of the invention is as follows: placing the pretreated sample, the lysis solution and an internal standard in the lysing zone of a detection tube; then well mixing the sample by a magnetizable mixing device in the lysis solution controlled by an external magnet, lysing the sample and releasing nucleic acid, so that magnetic nanobeads adsorb nucleic acid to complete extraction of nucleic acid; subsequently driving, by the external magnet, the magnetic nanobeads carrying nucleic acid to move downwards through the hydrophobic layer along the magnetic bead channel to the cleaning solution for cleaning, and continuously driving, using the external magnet, the magnetic nanobeads carrying the nucleic acid to move downwards through the hydrophobic layer along the magnetic bead channel to react in the reaction solution so as to elute the nucleic acid, in which the magnetic carrier carrying the biochemical reagent is transferred from the reagent storage chamber to the reaction solution in a magnetic control mode or a temperature control mode, and the biochemical reagent is dissolved and mixed in the reaction solution and then undergoes amplification reaction with nucleic acid; and finally detecting the nucleic acid of the sample by an external device using an optical detection method, thus realizing a plurality of steps of nucleic acid extraction, cleaning, elution and amplification reactions in the same detection reagent tube.

The invention claimed is:

1. A detection reagent tube for realizing a nucleic acid integrated detection method, the detection reagent tube comprising:

a main tube and one or more branch tubes provided at a lower end of the main tube, wherein a lysing zone, a cleaning zone and a plurality of separation plugs comprising at least a least a separation plug (3) and a second separation plug (4) which are sequentially disposed one on top of another in the main tube, wherein a reaction zone is provided in each branch tube and the second separation plug is positioned at a connection between the one or more branch tubes and the main tube;

a reagent storage chamber with a downward opening disposed in the second separation plug, a carrier for storing a reagent disposed in the reagent storage chamber and a hydrophobic sealing layer in the reagent storage chamber;

hydrophobic layers in a liquid or a solid phase disposed at each of the plurality of separation plugs; and a magnetic bead channel for magnetically carrying the nucleic acid to sequentially pass through each hydrophobic layer penetrating to the one or more branch tubes defined in an inner wall of the main tube.

2. The nucleic acid integrated detection reagent tube according to claim 1, wherein a magnetizable mixing device is provided in the reaction zone and/or the cleaning zone.

3. The nucleic acid integrated detection reagent tube according to claim 1, wherein the first separation plug comprises a plug, wherein a tapered surface is provided on an upper end of the plug and a bump is provided above the tapered surface.

4. The nucleic acid integrated detection reagent tube according to claim 3, wherein a plurality of arc-shaped convex surfaces are provided on a side wall of the plug and a channel is provided between adjacent arc-shaped convex surfaces.

5. The nucleic acid integrated detection reagent tube according to claim 1, wherein the second separation plug comprises a partition plate, a plurality of plug bodies corresponding to positions of the one or more branch tubes are arranged below the partition plate, a protrusion is arranged on an upper end of the partition plate; and a reagent storage chamber is disposed in each plug body.

6. The detection reagent tube for realizing the nucleic acid integrated detection method according to claim 1, wherein one or more branch tubes are provided at a lower part of the detection tube, the amplification reaction is performed in each branch tube, and one or more clusters of magnetic nanobeads carrying the nucleic acid are driven into the one or more branch tubes by the external magnet to react independently, so that nucleic acid from one sample can be simultaneously detected in one or more different reaction systems.

7. The detection reagent tube for realizing the nucleic acid integrated detection method according to claim 1, wherein a reagent storage chamber with a downward opening is disposed in the separation plug above the reaction solution, and a biochemical reagent is disposed in the reagent storage chamber, the biochemical reagent is stored on a carrier, and is sealed and protected by a hydrophobic sealing layer in the reagent storage chamber.

8. The detection reagent tube for realizing the nucleic acid integrated detection method according to claim 1, wherein the biochemical reagent is stored on a magnetic carrier and is sealed and protected by the hydrophobic sealing layer in the reagent storage chamber; when the reaction is needed, the biological reagent is driven by the external magnet to pass through the hydrophobic sealing layer and into the reaction solution, thus realizing the transferring of the biochemical reagent from the reagent storage chamber to the reaction solution.

9. The detection reagent tube for realizing the nucleic acid integrated detection method according to claim 1, wherein the biochemical reagent is stored on the carrier and is sealed and protected by the hydrophobic sealing layer composed of a hot melt substance; when the reaction is needed, a separation plug is heated in a temperature control mode, wherein the hot melt substance is heated and melted so that the biochemical reagent in the storage chamber can move out, thus realizing the transferring of the biochemical reagent from the reagent storage chamber to the reaction solution.

10. The detection reagent tube for realizing the nucleic acid integrated detection method according to claim 3, wherein one or more annular grooves are provided in a middle of the plug, and the one or more annular grooves divide the plug into two or more layers.

11. The detection reagent tube for realizing the nucleic acid integrated detection method according to claim 1, wherein the main tube is in a conical structure with a larger top and a smaller bottom, and a diameter of an upper end of the main tube is larger than a lower end of the main tube.

12. The detection reagent tube for realizing the nucleic acid integrated detection method according to claim 3, wherein a rib is provided at a lower end of the plug, an arc-shaped protrusion is provided in a side wall of the rib, the rib is provided with a plurality of cavities with downward openings, and the biochemical reagent is stored in the cavities.

13. The detection reagent tube for realizing the nucleic acid integrated detection method according to claim 1, wherein a positioning groove is provided between the plug bodies, and a positioning boss corresponding to the positioning groove are provided between the branch tubes; the positioning boss includes a conical protrusion arranged between branch tubes, and a positioning block is provided at the upper end of the conical protrusion.

14. The detection reagent tube for realizing the nucleic acid integrated detection method according to claim 1, there are a plurality of branch tubes.

15. The detection reagent tube for realizing the nucleic acid integrated detection method according to claim 1, wherein a separation layer is provided in the reagent storage chamber.

* * * * *